United States Patent [19]

Breuer

[11] Patent Number: 5,039,703

[45] Date of Patent: Aug. 13, 1991

[54] METHOD FOR TREATING INFLAMMATORY BOWEL DISORDERS

[76] Inventor: Richard I. Breuer, 822 Lincoln St., Evanston, Ill. 60201

[21] Appl. No.: 438,297

[22] Filed: Nov. 16, 1989

[51] Int. Cl.$^5$ .............................................. A61K 31/19
[52] U.S. Cl. .................................... 514/557; 514/425
[58] Field of Search ................................ 514/557, 925

[56] References Cited

PUBLICATIONS

W. E. W. Roediger, "The Colonic Epithelium in Ulcerative Colitis: An Energy-Deficiency Disease", The Lancet, Oct. 4, 1980, pp. 712-715.

Harig et al., "Treatment of Diversion Colitis with Short Chain Fatty Acid (SCFA) Irrigation", Abstracts of Papers, 88th Annual Meeting of the American Gastro--Enterological Association, May 1987, p. 1425.

Schilli et al., "Comparison of the Composition of Faecel Fluid in Crohn's Disease and Ulcerative Colitis", Gut. 1982, 23, 326-332.

Vernia et al., "Organic Anions and the Diarrhea of Inflammatory Bowel Disease" Digestive Diseases and Sciences, vol. 33, No. 11 (Nov. 88), pp. 1353-1358.

Vernia et al., "Fecal Lactate and Ulcerative Colitis", Gastroenterology, Dec. 88, vol. 95, No. 6, pp. 1564-1568.

Harig et al., "Treatment of Diversion Colitis with Short-Chain-Fatty Acid Irrigation", *The New England Journal of Medicine*, Jan. 5, 1989, vol. 320, No. 1, pp. 23-28.

*Primary Examiner*—Leonard Schenkman
*Attorney, Agent, or Firm*—Dressler, Goldsmith, Shore, Sutker & Milanamow, Ltd.

[57] ABSTRACT

A method for the treatment of inflammatory bowel disorders, together with a pharmaceutical composition comprising short chain fatty acids that is useful therein, is described in this invention. The administration of short chain fatty acids of about 2 to about 6 carbon-length to patients afflicated with inflammatory bowel disorders is shown to effectively alleviate the symptoms of the treated disorder.

8 Claims, 1 Drawing Sheet

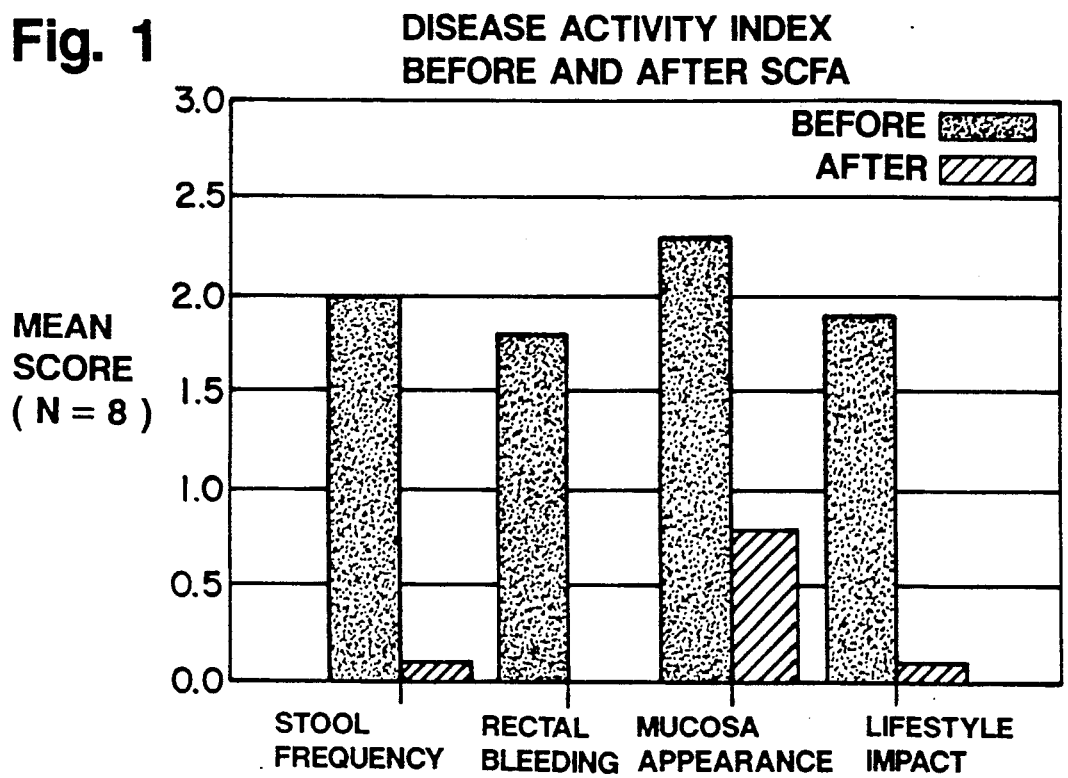
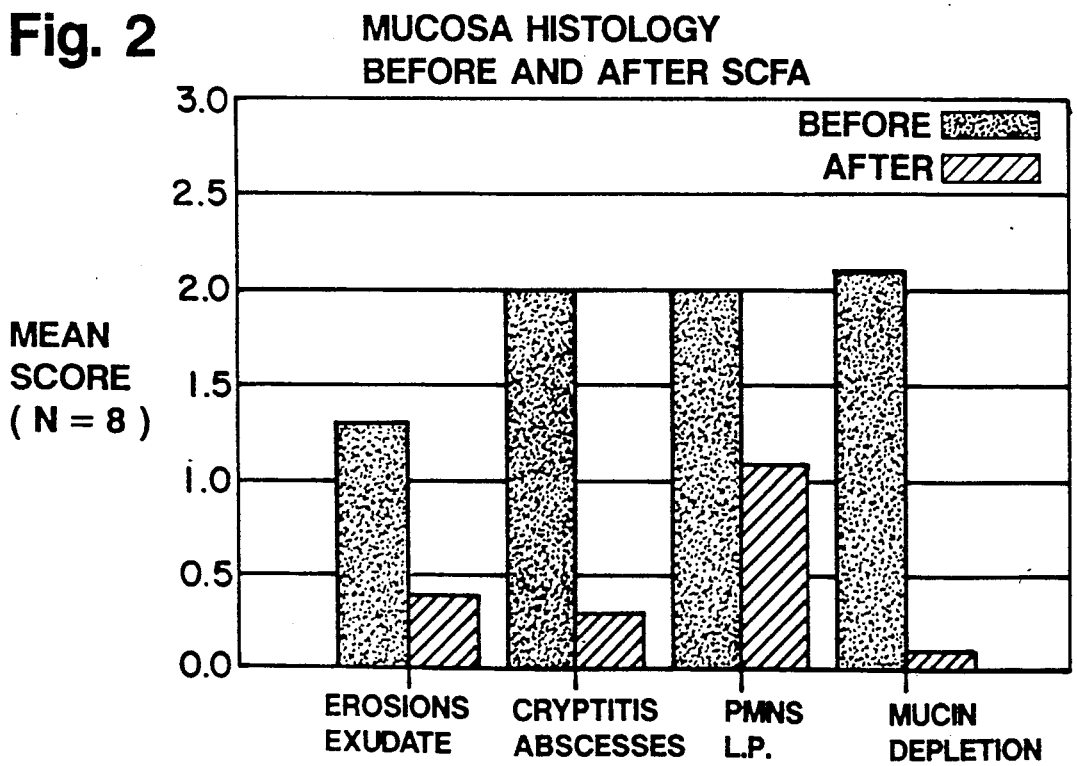

METHOD FOR TREATING INFLAMMATORY BOWEL DISORDERS

TECHNICAL FIELD

The present invention is directed to a method of treating inflammatory bowel disorders and to compositions useful therein.

BACKGROUND OF THE INVENTION

Inflammatory bowel disorders (IBD) encompass a spectrum of overlapping clinical diseases that appear to lack a common etiology. IBD, however, are characterized by chronic inflammation at various sites in the gastrointestinal (GI) tract. Illustrative IBD are regional enteritis (or Crohn's disease), idiopathic ulcerative colitis and infectious colitis. Most hypotheses regarding the pathogenesis of IBD concern the implication of immunologic, infectious and dietary factors.

Short chain fatty acids (SCFA) are normal components of colonic fluid. SCFA are the metabolic end product of anaerobic bacterial fermentation of carbohydrates.

Absorption of SCFA in the colon aids salt and water absorption, maintains a neutral-to-alkaline pH in the colonic lumen and prevents diarrhea which would otherwise occur if unaltered carbohydrates remain in the colon where they would act as an osmotic cathartic. SCFA absorbed from the fecal stream provide up to 85% of the energy metabolism for the cells of the distal colon and about 60% for those of the proximal colon.

The concentration of SCFA in the colonic fluid of patients with severe colitis is lower than in normal patients, and the level of SCFA in patients with severe ulcerative colitis is lower than that in patients with Crohn's disease. Vernia et al., Gastroenterology 95:1564–1568 (1988); Vernia et al., Dig. Dis. Sci., 33:1353–1358 (1988).

Studies on isolated colonic epithelial cells obtained from patients with acute and quiescent ulcerative colitis and from normal control patients have suggested that ulcerative colitis is an energy-deficient syndrome. The oxidation of one SCFA, butyric acid, to carbon dioxide was shown to be significantly lower by cells from colitis patients than in cells from normal individuals. Roediger, Lancet (Oct. 4, 1980). This result is hypothesized to be due to the lower concentration of coenzyme A present in mucosal cells of ulcerative colitis patients.

Excessively decreased concentrations of SCFA, to almost absent levels, have been observed in another colonic condition, diversion colitis (DC), which develops in response to the surgical exclusion of a portion of the colon from the fecal stream of colonic fluid. Harig et al., N. Eng. J. Med. 320:23–28 (1989). Harig et al. reported that irrigation of the colonic mucosa of DC patients with a solution of SCFA at concentrations close to those found in normal fecal water markedly improved the inflammatory process and could reverse the inflammatory condition.

The present invention relates to the utilization of SCFA in treating inflammatory bowel disorders such as ulcerative colitis and Crohn's disease.

SUMMARY OF THE INVENTION

The present invention is directed to a method of treating inflammatory bowel disorders and to pharmaceutical compositions comprising short chain fatty acids that are useful therein.

In the present invention, an inflammatory bowel disorder, such as idiopathic ulcerative colitis or Crohn's disease, is treated in a patient by administering, such as by rectal enema, to the patient a therapeutically effective amount of a composition comprising SCFA, or their pharmaceutically acceptable salts, for a time period sufficient to alleviate the symptoms of the disorder. The administered composition contains at least one SCFA at a concentration that is elevated over (or higher than) the normal physiological concentration for that SCFA. For example, the concentration of butyric acid in the composition can be about twice that which is normally present in colonic fluid.

Illustrative SCFA utilized in the method of the present invention are acetic acid, propionic acid, n-butyric acid, isobutyric acid, valeric acid, isovaleric acid and pharmaceutically acceptable salts thereof, such as the sodium and potassium salts.

A pharmaceutical composition of the present invention contains SCFA, or pharmaceutically acceptable salts thereof, together with a pharmaceutically acceptable carrier, where the concentration of at least one fatty acid in the composition is higher than its normal physiological concentration in colonic fluid. Each SCFA is dissolved or dispersed in the composition at a concentration of about 20 to about 100 milliequivalents/liter (mEq/liter). Additional therapeutic or pharmaceutical compounds can, optionally, be present in the composition. An illustrative pharmaceutical composition of the present invention contains about 80 mEq/liter of sodium acetate, about 30 mEq/liter of sodium propionate and about 40 mEq/liter of n-butyric acid dissolved or dispersed in saline that has been adjusted to pH 7.

BRIEF DESCRIPTION OF THE DRAWINGS

FIG. 1 is a bar graph of the Disease Activity Index for the listed criteria for eight patients determined before treatment (shaded) and one week after a six-week treatment period was terminated (open-hatched) with short chain fatty acid compositions.

FIG. 2 is a bar graph of the mucosal histology of the colon for the listed features for eight patients determined before treatment (shaded) and one week after a six-week treatment period was terminated (open-hatched) with short chain fatty acid compositions.

DESCRIPTION OF PREFERRED EMBODIMENTS

The present invention is directed to a method of treating inflammatory bowel disorders and to pharmaceutical compositions of short chain fatty acids (SCFA) that are utilized in the present treatment method.

Inflammatory bowel disorders (IBD) such as Crohn's disease, ulcerative colitis and infectious colitis have been shown to afflict patients with a primary mucosal defect in the absorption of sodium, chloride and water from the colon. Patients with IBD have fecal volumes several times greater than normal with markedly deranged electrolyte patterns. The level of Krebs cycle anions, such as lactate and succinate, in IBD fecal water is higher than in normal patients. Vernia et al. Dig. Dis. Sci. 83:1353–1358 (1988).

As used herein, the term "short chain fatty acids" or "SCFA" refers to $C_2$ to $C_6$ carbon-length fatty acids and include acetic, propionic, butyric, isobutyric, valeric and isovaleric acid and the like.

As used herein, the term "pharmaceutically acceptable salts" refers to non-toxic alkali and alkaline earth metal salts and include sodium, calcium, potassium and magnesium salts and the like.

A carrier or diluent is a material useful for administering the SCFA of the present invention, and must be "pharmaceutically acceptable" in the sense of being compatible with the composition and not deleterious to the recipient thereof. Thus, as used herein, the phrase "pharmaceutically acceptable" refers to molecular entities that do not produce an allergic or similar untoward reaction when administered to a patient.

The concentration of SCFA in the fecal water of patients with severe ulcerative colitis is lower than that present in normal patients. In fact, the increased concentrations of lactate and succinate in ulcerative colitis patients are quantitatively matched by the decreased concentration of acetate, propionate and butyrate in these patients, suggesting a shift in bacterial metabolism toward production of the Krebs cycle anions. Perman et al., J. Clin. Invest. 67:632–650 (1981). In patients with severe colitis, SCFA concentrations are markedly reduced. Vernia et al., Dig. Dis. Sci. 33:1353–1358 (1988).

In the present invention, a patient having an IBD is treated by a therapeutically effective amount of a composition comprising SCFA, or pharmaceutically acceptable salts thereof, for a time period sufficient to alleviate the symptoms of the disorder. The administered composition preferably contains a physiologically elevated concentration of at least one SCFA, such as n-butyric acid. For example, the administered composition can contain n-butyric acid at a concentration in excess of the normal concentration of n-butyric acid in fecal water, that is, n-butyric acid is present at a physiologically elevated concentration.

In a preferred embodiment, a patient is administered, by rectal enema, a unit dosage of a composition containing about 80 mEq/liter of sodium acetate, about 30 mEq/liter of sodium propionate and about 40 mEq/liter of n-butyric acid, dissolved in saline and adjusted to about pH 7, twice daily for a time period sufficient to alleviate the symptoms of the IBD.

As used herein, the term "unit dosage" refers to a predetermined quantity of the SCFA composition of the present invention calculated to produce the desired therapeutic effect in the patient. A preferred unit dosage of the present invention is about 50 to about 100 ml, administered twice daily to a patient.

The composition utilized in the method of the present invention can, optionally, contain additional therapeutic or pharmaceutical compounds such as antidiarrheal agents, antibiotics, topical anesthetics, stool softeners and lubricants.

In a particularly preferred embodiment, the method of the present invention is employed to treat general left-sided colitis, idiopathic ulcerative colitis, Crohn's disease and infectious colitis.

A pharmaceutical composition of the present invention contains SCFA, or pharmaceutically acceptable salts thereof, dissolved or dispersed in a pharmaceutically acceptable carrier, such as saline. In a preferred embodiment, at least one SCFA in the composition is present at a physiologically elevated concentration, as described hereinbefore.

In a particularly preferred embodiment, a pharmaceutical composition of the present invention contains about 80 mEq/liter of sodium acetate, about 30 mEq/liter of sodium propionate and about 40 mEq/liter of n-butyric acid dissolved or dispensed in saline, and the composition is adjusted to about pH 7.

The present invention is further illustrated by the following Examples which are not intended to limit the scope of the invention.

EXAMPLE 1

Eight patients suffering from left-sided colitis were treated for six weeks by the rectal administration of a SCFA solution (100 ml) twice daily. The solution contained sodium acetate (80 mEq/liter), sodium propionate (30 mEq/liter) and n-butyric acid (40 mEq/liter) in saline with the pH adjusted to pH 7 with sodium hydroxide.

All of the patients were refractory in that each had had prior IBD attacks. Two patients were on stable dosages of systemic steroids for at least three months, and two other patients were on the same dose of sulfasalazine for at least two months. The other four patients were on no medication. Results were assessed by changes in a Disease Activity Index (DAI) and mucosal histology. The DAI and mucosal histology index, respectively, are the sum of the individual gradings as described in TABLE I.

TABLE I

| Disease Activity Index |
|---|
| 1. Stool frequency |
|     0 = Normal |
|     1 = 1–2 stools/day > normal |
|     2 = 3–4 stools/day > normal |
|     3 = >4 stools/day > normal |
| 2. Rectal bleeding |
|     0 = None |
|     1 = Streaks of blood |
|     2 = Obvious blood |
|     3 = Mostly blood |
| 3. Mucosal appearance |
|     0 = Normal |
|     1 = Mild friability |
|     2 = Moderate friability |
|     3 = Exudation, spontaneous bleeding |
| 4. Impact of symptoms on lifestyle or activities of daily living |
|     0 = No impact on lifestyle |
|     1 = Occasional interference with lifestyle or activities of daily living |
|     2 = Frequent or significant impact on lifestyle or activities of daily living |
|     3 = Unable to participate in usual activities |
| Mucosal Histology Index |
| Gradings:   0 = Normal |
|                1 = Mild |
|                2 = Moderate |
|                3 = Severe |
| Features:   Cryptitis/abscesses |
|                Erosion/exudate |
|                Polymorphonuclear leukocytes (PMNs) in the lamina propria |
|                Glandular mucin depletion |

The results are shown in FIGS. 1 and 2. All eight patients were judged to be "much improved." Rectal bleeding had stopped in all eight patients and normal stool frequency had returned in seven patients. The average total DAI improved from 7.9, at the beginning of the observation period, to 1.1 at the end of the study. No toxicity was noticed and only two patients had any relapse of symptoms, which were easily controlled by repeated treatment.

All eight patients showed a marked improvement in mucosal histology (FIG. 2) after treatment.

EXAMPLE 2

Six of the patients treated by the protocol described in Example 1 had fecal SCFA analyses conducted on 24-hour fecal fluid specimens collected prior to onset of therapy and approximately one week after ending therapy.

Three patients presented no significant change in fecal SCFA. The remaining three patients had a definite change with an increase of 1.5- to 2-fold in their pretreatment values for fecal SCFA. Each of these three patients had a doubling of butyrate concentration and have experienced dramatic clinical improvement.

These results suggest that, with improvement in the inflammatory process, the handling of endogenous SCFA by the patients returns to normal.

EXAMPLE 3

The results for five of the patients treated in Example 1 are shown in TABLES II and III.

The average DAI improved from 8, at the beginning of the observation period, to 1 at the end of the study. Four of the patients showed marked improvement in mucosal histology.

One patient had a relapse of symptoms that were easily controlled by administering once daily irrigation of the SCFA solution every other day.

The SCFA levels in two patients were measured and it was found that the concentrations of acetate, propionate and butyrate were increased 1.5- to 2-fold in the fecal water collected one week after the end of treatment as compared to pretreatment values.

The foregoing description and the Examples are intended as illustrative and are not to be taken as limiting. Still other variations within the spirit and scope of this invention are possible and will readily present themselves to those skilled in the art.

TABLE II

| Patient | Stool Frequency B | Stool Frequency A | Rectal Bleed B | Rectal Bleed A | Mucosal Appearance B | Mucosal Appearance A | Lifestyle Impact B | Lifestyle Impact A | Total Score B | Total Score A | Physician's Global Assessment |
|---|---|---|---|---|---|---|---|---|---|---|---|
| 1 | 2 | 0 | 2 | 0 | 2 (15 cm.) | 0 | 2 | 0 | 8 | 0 | Much Improved |
| 2 | 2 | 0 | 0 | 0 | 2 (>50 cm.) | 1 | 2 | 0 | 6 | 1 | Much Improved |
| 3 | 3 | 1 | 2 | 0 | 2 (40 cm.) | 1 | 2 | 0 | 9 | 2 | Much Improved |
| 4 | 0 | 0 | 2 | 0 | 3 (15 cm.) | 1 | 2 | 0 | 7 | 1 | Much Improved |
| 5 | 2 | 0 | 2 | 0 | 3 (45 cm.) | 0 | 2 | 0 | 9 | 0 | Much Improved |

B = Before Treatment
A = One Week After Treatment

TABLE III

| Patient | Erosions Exudate B | Erosions Exudate A | Cryptitis Abscesses B | Cryptitis Abscesses A | PMNs LP B | PMNs LP A | Mucin Depletion B | Mucin Depletion A | Total B | Total A |
|---|---|---|---|---|---|---|---|---|---|---|
| 1 | 1 | 0 | 1 | 0 | 0 | 0 | 1 | 0 | 3 | 0 |
| 2 | 2 | 2 | 1 | 0 | 3 | 3 | 2 | 0 | 8 | 5 |
| 3 | 1 | 0 | 3 | 0 | 2 | 0 | 2 | 0 | 8 | 0 |
| 4 | 1 | 0 | 2 | 0 | 1 | 2 | 2 | 1 | 6 | 3 |
| 5 | 2 | 0 | 2 | 0 | 3 | 1 | 3 | 0 | 10 | 1 |

B = Before Treatment
A = One Week After Treatment

We claim:

1. A method of treating a non-diversion inflammatory bowel disorder comprising administering to a patient having said bowel disorder a therapeutically effective amount of a composition comprising short chain fatty acids or pharmaceutically acceptable salts thereof for a time period sufficient to alleviate the symptoms of said bowel disorder, said composition containing a physiologically elevated concentration of at least one of said fatty acids.

2. The method of claim 1 wherein said short chain fatty acids are selected from the group consisting of acetic acid, propionic acid, butyric acid, isobutyric acid, valeric acid, isovaleric acid and pharmaceutically acceptable salts thereof.

3. The method of claim 1 wherein said patient is administered a composition comprising about 80 mEq/liter of sodium acetate, about 30 mEq/liter of sodium propionate and about 40 mEq/liter of n-butyric acid, adjusted to a pH of about 7.

4. The method of claim 1 wherein said administration is by rectal enema.

5. The method of claim 1 wherein said non-diversion inflammatory bowel disorder is idiopathic ulcerative colitis.

6. The method of claim 1 wherein said non-diversion inflammatory bowel disorder is Crohn's disease.

7. The method of claim 1 wherein said non-diversion inflammatory bowel disorder is severe ulcerative colitis.

8. A method for treating a non-diversion inflammatory bowel disorder selected from the group consisting of Crohn's disease and ulcerative colitis comprising administering to a patient in need of such treatment a therapeutically effective amount of a composition comprising a physiologically elevated concentration of at least one short chain fatty acid or a pharmaceutically acceptable salt thereof for a time period sufficient to alleviate the symptoms of said bowel disorder.

* * * * *